United States Patent [19]
Iida et al.

[11] Patent Number: 5,235,983
[45] Date of Patent: Aug. 17, 1993

[54] ULTRASONIC IMAGING APPARATUS

[75] Inventors: Atsuo Iida; Takuya Noda, both of Kawasaki, Japan

[73] Assignee: Fujitsu Limited, Kawasaki, Japan

[21] Appl. No.: 846,336

[22] Filed: Mar. 6, 1992

[30] Foreign Application Priority Data

Mar. 8, 1991 [JP] Japan .................................. 3-42132
Mar. 2, 1992 [JP] Japan .................................. 4-44757

[51] Int. Cl.$^5$ .............................................. A61B 8/00
[52] U.S. Cl. .......................... 128/660.07; 128/661.01; 128/660.06; 73/625
[58] Field of Search ............. 128/660.06, 660.07, 128/661.01; 73/597, 605, 629, 625

[56] References Cited

U.S. PATENT DOCUMENTS

| | | | |
|---|---|---|---|
| 4,458,533 | 7/1984 | Borbugh | 73/625 |
| 4,564,019 | 1/1986 | Miwa | 128/660.06 |
| 4,700,573 | 10/1987 | Savord | 73/625 |

*Primary Examiner*—Kyle L. Howell
*Assistant Examiner*—George Manuel
*Attorney, Agent, or Firm*—Staas & Halsey

[57] ABSTRACT

An ultrasonic imaging apparatus for obtaining a tomogram image of an object to be diagnosed on a monitor includes electroacoustic transducers, a phasing unit, a phase detection unit, and an adding unit. The electroacoustic transducers are positioned in aligned relationship along a surface of the object, emit ultrasonic waves which penetrate the object, detect the ultrasonic waves reflected from the object and convert the reflected and detected waves to electrical detection signals. A phasing unit is connected to the electroacoustic transducers and receives the detection signals, delays them in accordance with delay amounts previously set therein and determined in accordance with the respective distances between the electroacoustic transducers and the object, and phase adjusts same to produce phase-matched detection signals. A phase detection unit is connected to the electroacoustic transducers and the phasing unit for detecting the phase errors contained in the detection signals output by the electroacoustic transducers or the phase-matched detection signals output by the phasing unit, and corrects the delay amount previously set in the phase unit in accordance with the phase error. The phase detection unit further comprises first and second binary units for binarizing the detection signals to detect the phase error contained in the detection signals. An adding unit connected to the phasing unit accumulates the phase-matched detection signals.

11 Claims, 15 Drawing Sheets

ULTRASONIC IMAGING APPARATUS

BACKGROUND OF THE INVENTION

1. Field of the Invention

The present invention relates to an ultrasonic imaging apparatus for obtaining a tomogram image of an object by using ultrasonic waves. The present invention is used mainly as a medical instrument for diagnosis.

2. Description of the Related Art

Recently, an ultrasonic imaging apparatus is widely used as a medical instrument for obtaining a tomogram image of an object, for example internal organs of a human body. Basically, the ultrasonic image apparatus has a plurality of electroacoustic transducers positioned in aligned relationship along the surface of the object. The electroacoustic transducers emit ultrasonic waves to the object and detect the ultrasonic waves reflected therefrom. The detected ultrasonic waves are added to each other, after a phasing process (i.e., which matches the phases of the detection signals) in accordance with a predetermined delay process for ultrasonic waves, to obtain the phased detection signal, i.e., a phase-matched, and thus strengthened, detection signal. After the above processes, it is possible to obtain an image signal on one scan line focused to one particular point on the scan line in the object. When electrically scanning the electroacoustic transducers, the focused point is straightly scanned (i.e., scanned linearly with parallel scan lines) so that it is possible to obtain the tomogram image of the object. Further, when controlling the time difference (also referred to below as the amount of delay), the focused point is curvedly scanned (i.e., as in a sector scan, with radial scan lines) so that it is possible to obtain the tomogram image of the object.

In this case, a propagation speed of the ultrasonic wave is slightly different within the object caused by the medium forming the object. That is, the propagation speed for the adipose tissue is different from that of the muscle tissue. Accordingly, the delay process is very important for adjusting the different propagation speeds of the ultrasonic waves to obtain a clear tomogram image of the object. That is, when the propagation speed is not uniform within the object, it is impossible to obtain the clear tomogram image of the object. Accordingly, it is necessary to provide means for preventing the deterioration of the tomogram image caused by nonuniformity of the propagation speed of the ultrasonic waves within the object.

SUMMARY OF THE INVENTION

The object of the present is to provide an ultrasonic imaging apparatus enabling the prevention of deterioration of the tomogram image caused by nonuniformity of the propagation speed within the object and thereby enabling the obtaining of a high precision tomogram image.

In accordance with the present invention, there is provided an ultrasonic imaging apparatus for obtaining a tomogram image of an object to be diagnosed on a monitor, including:

electroacoustic transducers provided in a line (i.e., positioned in aligned relationship) along a surface of the object, emitting ultrasonic waves to the object, detecting the ultrasonic waves reflected therefrom, and converting them to electric signals used as detection signals;

a phasing unit operatively connected to the electroacoustic transducers for receiving the detection signals, delaying them in accordance with the respective distances between the electroacoustic transducers and the object, and phasing them to produce phase-matched detection signals;

a phase detection unit operatively connected to the electroacoustic transducers and the phasing unit for detecting the phase errors contained in the detection signals output from the electroacoustic transducers or the phasing unit and correcting the amount of delay previously set in the phasing unit in accordance with the phase errors; the phase detection unit further comprising first and second binary units for binarizing the detection signals thereby to detect the phase errors contained in the detection signals; and an adding unit operatively connected to the phasing unit to accumulate the detection signals phased by the phasing unit.

In the preferred embodiment, the phase detection unit further includes first and second shift registers connected to the corresponding binary units for sequentially latching and shifting the binary signals, the first shift register having more latch units than the second shift register, and an error detection unit for detecting cross-correlation values for the binary signals from the first and second shift registers, and further detecting any phase error of the detection signals input to the first and second binary units so that phase errors for all detection signals are detected by accumulating the phase errors.

In another preferred embodiment, the phase detection unit further includes an input delay unit connected to the second binary unit for delaying the respective binary signals and outputting the delayed binary signals to the second shift register to correct the phase error detected by the error detection unit in accordance with the amount of delay at the input delay unit.

In still another preferred embodiment, the error detection unit includes adder units and a decision unit; the former are provided in the same number as that of the latch units of the second shift register thereby to receive both latch signals from the first and second shift registers, and to accumulate the latch signals when both latch signals indicate the same level; the latter receives the accumulated latch signals and determines the maximum value from the accumulated latch signals.

In still another preferred embodiment, the apparatus further includes a signal generating unit operatively connected to the phase detection unit for generating and supplying a reference signal to one of two binary units.

In accordance with another aspect of the present invention, there is provided an ultrasonic imaging apparatus for obtaining a tomogram image of an object to be diagnosed on a monitor, including:

electroacoustic transducers are provided in alignment and positioned along a surface of the object, for emitting ultrasonic waves to the object, detecting the ultrasonic waves reflected therefrom, and converting them to electric signals used as detection signals;

a phasing unit operatively connected to the electroacoustic transducers for receiving the detection signals, delaying them in accordance with the distance between the electroacoustic transducers and the object, and phasing them to produce phase-matched detection signals;

a reference signal generating unit operatively connected to the phase detection unit for generating a reference signal; a phase detection unit operatively contacted to the electroacustic transducers and the phasing unit for detecting the phase error contained in the detection signals output from the electroacoustic transducers or the phasing unit and correcting the amount of delay previously set in the phase unit in accordance with the detected phase error; and an adding unit operatively connected to the phasing unit to accumulate the phase-matched detection signals output by the phasing unit, the phase detection unit further including first and second binary units for binarizing the detection signals, thereby to detect the phase error contained in the detection signals and of which one binary unit inputs the detection signal and the other binary unit inputs the reference signal having the same frequency as that of the detection signal; a multiplication unit operatively connected to the first and second binary units for multiplying the respective binary signals from the first and second binary units; and a detection unit operatively connected to the multiplication unit for extracting direct current components contained in the binary signal multiplied by the multiplication unit thereby to detect the phase error of the detection signals input to the two binary units.

Further, in the preferred embodiment, the first and second binary units set a threshold value for binarizing the detection signals to approximately the peak of the thermal noise level of the electroacoustic transducer. In this case, preferably, the first and second binary units output logic "1" when the detection signal is higher than the thermal noise level, and output logic "0" when the detection signal is equal to or lower than the thermal noise level.

DESCRIPTION OF THE PREFERRED EMBODIMENTS

Before describing the preferred embodiments, an explanation will be given of a conventional ultrasonic imaging apparatus.

Figure 1:
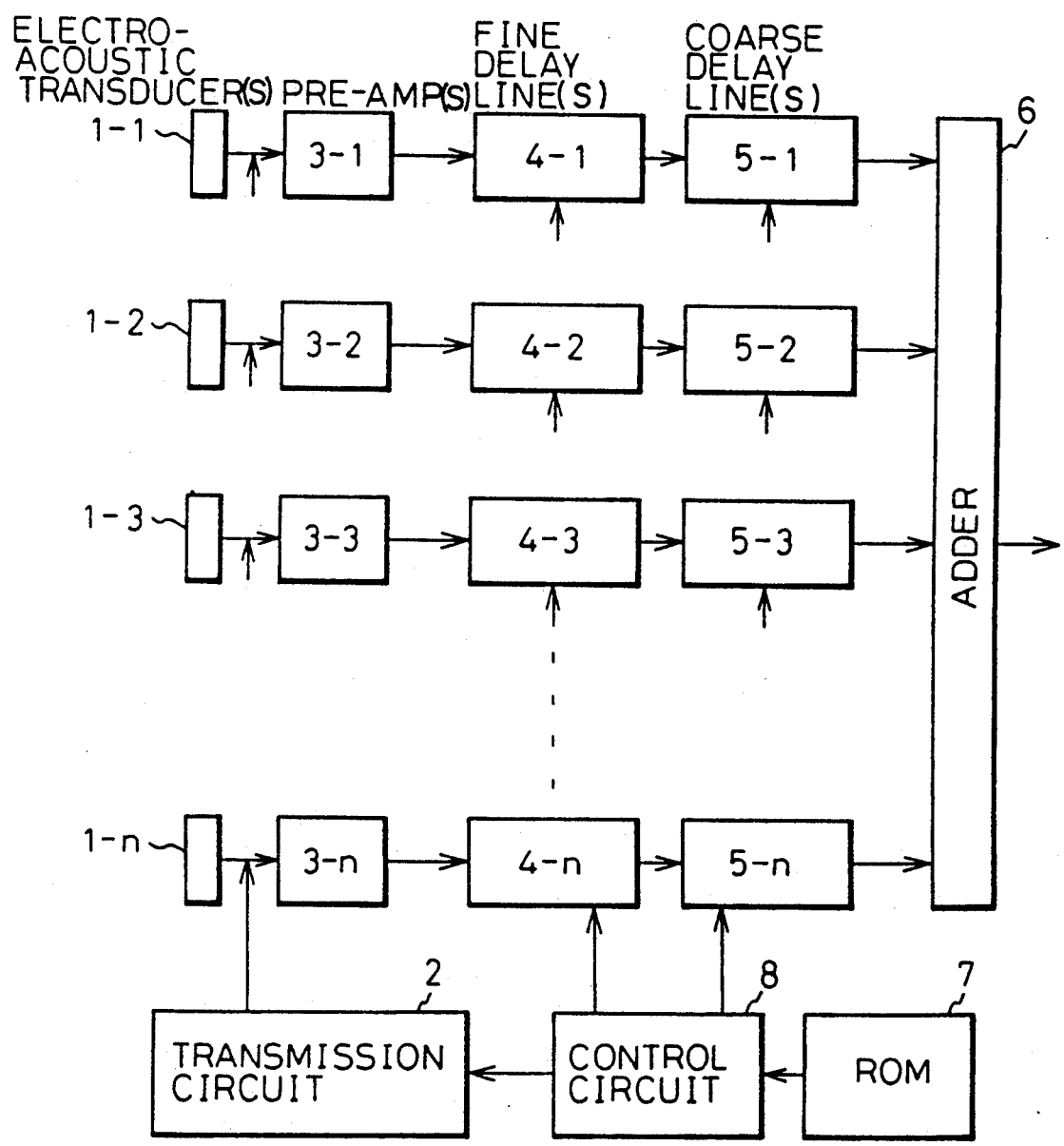
FIG. 1 is a schematic block diagram of a conventional ultrasonic imaging apparatus.

FIG. 1 is a schematic block diagram of a conventional ultrasonic imaging apparatus. This ultrasonic imaging apparatus is known and disclosed in documents, for example, (1) Japanese Unexamined Patent Publication (KOKAI) No. 53-28989, and (2) Japanese Unexamined Patent Publication (KOKAI) No. 54-96286. The former application corresponds to U.S. Application (718721) by Richard D. Belling, filed on Aug. 30, 1976, and the latter corresponds to U.S. Application (862454) by Samual H. Masrak, filed on Dec. 20, 1977.

In FIG. 1, reference numbers 1-1 to 1-n denote electroacoustic transducers, 2 a transmission circuit, 3-1 and 3-n pre-amplifiers, 4-1 to 4-n fine delay lines, 5-1 to 5-n coarse delay lines, 6 an adder, 7 a read only memory (ROM), and 8 a control circuit.

The electroacoustic transducers 1-1 to 1-n are provided in a line (i.e., are aligned) along the surface of the object, and the electroacoustic transducers 1-1 to 1-n emit the ultrasonic waves to the object and detect the ultrasonic waves reflected from the object (below, detection signal). The transmission circuit 2 generates electric pulses and supplies same in parallel to the electroacoustic transducers 1-1 to 1-n to control the emission of the ultrasonic waves. The pre-amplifiers 3-1 to 3-n amplify the respective detection signals from the electroacoustic transducers 1-1 to 1-n. The fine delay lines 4-1 to 4-n are formed by LC (inductor and capacitor) circuits for delaying the detection signals from the respective pre-amplifiers based on an adjustable amount of delay. The coarse delay lines 5-1 to 5-n are also formed by LC circuits and function for providing a fixed amount of delay. By these delay lines, the detection signals are phased. The adder 6 adds all of the outputs from the respective coarse delay lines 5-1 to 5-n to obtain the tomogram of the object. The ROM 7 stores data of the fine and coarse amounts of the delay previously determined in accordance with the difference of the distance between each electroacoustic transducer and the focused point. The amount of delay is shown by the formula (1) explained hereinafter. The control circuit 8 determines the fine delay amount and the coarse delay amount in accordance with the data stored in ROM 7.

Figure 2:
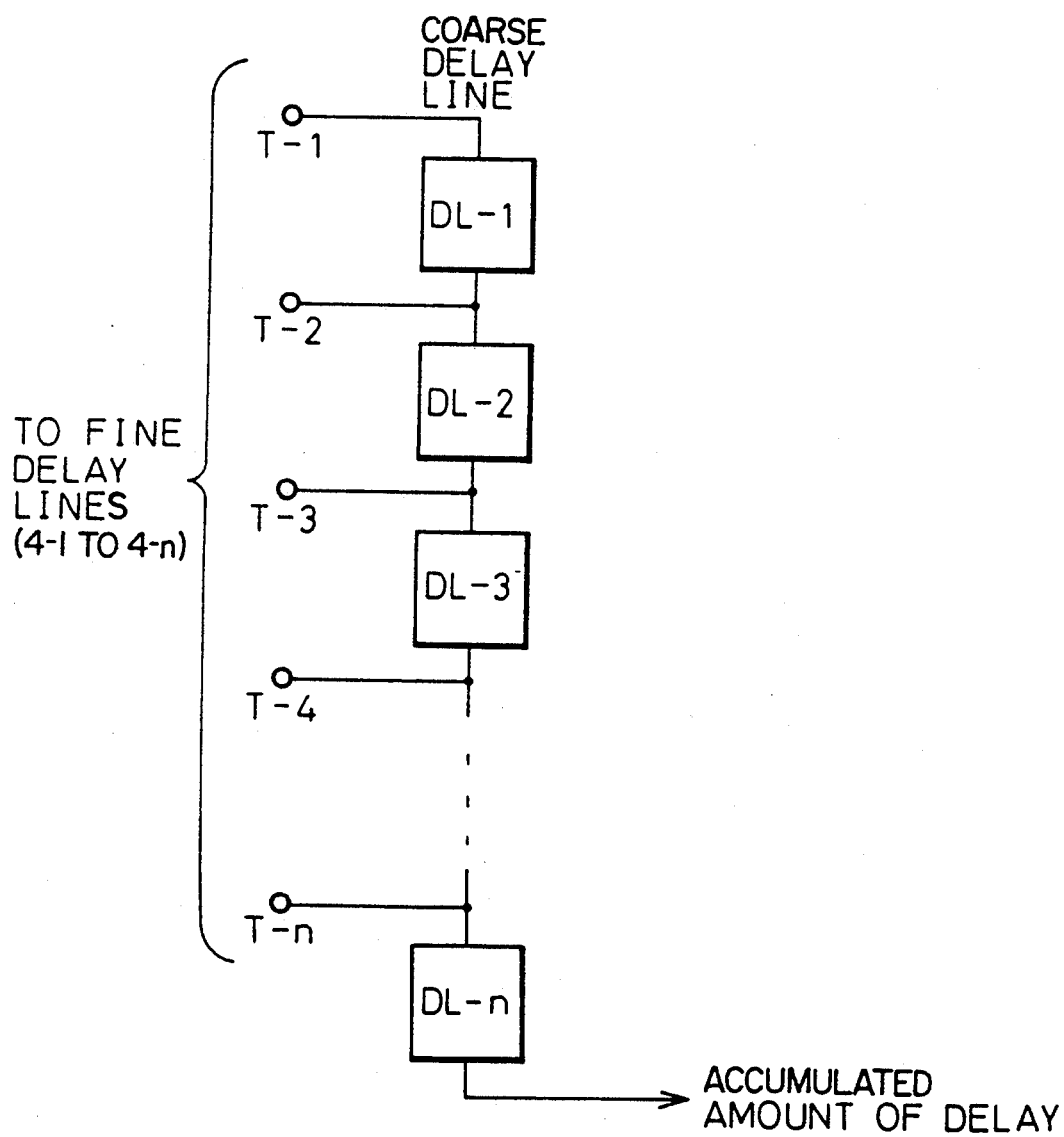
FIG. 2 is a schematic block diagram of a conventional coarse delay line shown in FIG. 1.

FIG. 2 is a schematic block diagram of a conventional coarse delay line of the type shown in FIG. 1. The coarse delay line comprises fixed delay lines DL-1 to DL-n having corresponding taps T-1 to T-n connected to the respective fine delay lines 4-1 to 4-n and functions to simultaneously perform delay and adding operations. In this case, each of delay lines DL-1 to DL-n has the same amount of delay, $\Delta t$, so that the total amount of the delay Ti of the fixed delay line can be expressed by the formula (2) as explained hereinafter. Since all amounts of delay are accumulated by these delay lines DL-1 to DL-n, it is possible to delete the adder 6 shown in FIG. 1.

Figure 3:
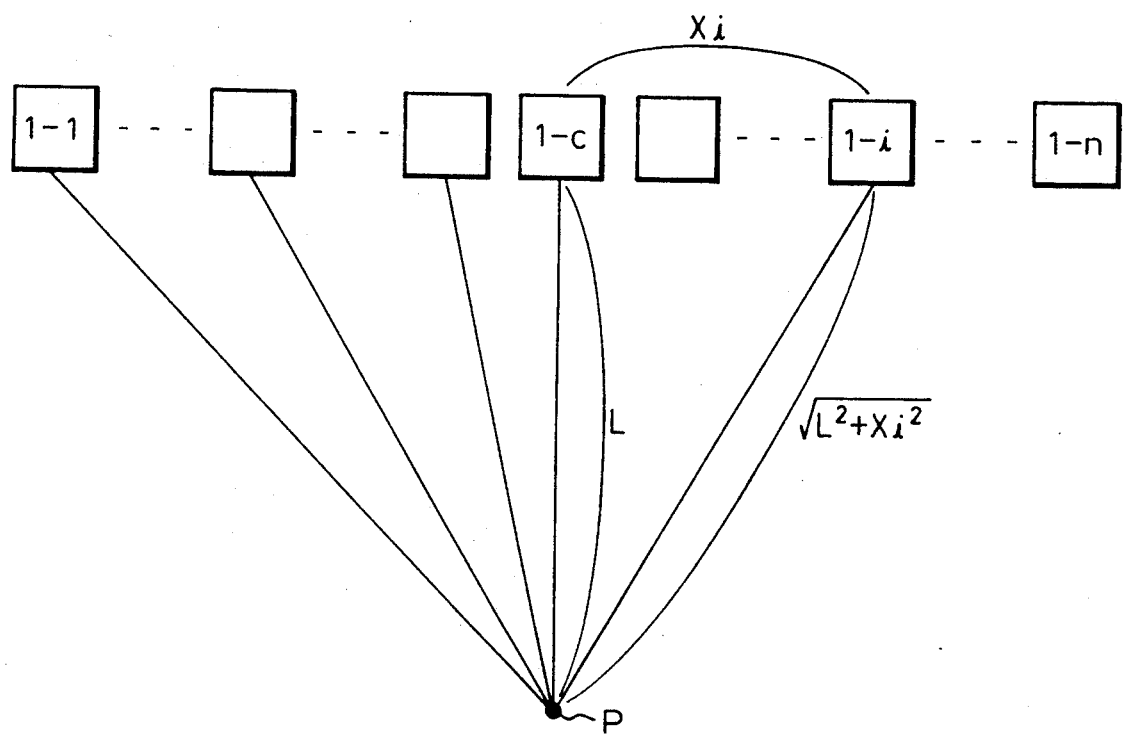
FIG. 3 is a view for explaining amount of delay.

FIG. 3 is a view explaining the amount of delay. 1-1 to 1-n denote electroacoustic transducers, 1-c denotes a center transducer and 1-i denotes the transducer away from the center transducer 1-c by distance Xi. "P" denotes a common focus point of the emission of all transducers 1-1 to 1-n and this focused point P is located at a distance L from the center transducer 1-c. In this case, the amount of delay $\tau i$ at the transducer 1-i is given as the following formula.

$$\tau i = \tau 0 - (\sqrt{(L^2 + Xi^2)} - L)/C \quad (1)$$

where C denotes the speed of the ultrasonic waves and $\tau 0$ denotes a constant value, the value $\tau i$ of which becomes positive.

Accordingly, the detection signal from the electroacoustic transducer 1-i is phased by the amount of delay $\tau i$. Similarly, all detection signals are phased by respectively corresponding amounts, and after a phasing process by the delay lines, all phased detection signals are added by the adder 6. As is obvious from the formula (1), since the distance between the electroacoustic transducer 1-i and the focused point P is longer than the distance between the electroacoustic transducer 1-c and the focused point P, the amount of the delay of the transducer 1-i is set to a value smaller than that of the transducer 1-c. As explained above, when electrically scanning the electroacoustic transducers, the focused point is straightly scanned so that it is possible to obtain the tomogram of the object. When controlling the amount of delay, the focused point is curvedly scanned so that it is possible to obtain the tomogram of the object.

Further, the amount of delay Ti at each of the coarse delay lines 5-1 to 5-n is expressed by the following formula.

$$Ti = int(\tau i/\Delta \tau) \times \Delta \tau \quad (2)$$

where, $\Delta \tau$ is a fixed delay amount per unit length of the coarse delay line (so-called quantumized error), and "int" is a positive integer.

The amount of delay "ti" at each of the fine delay lines 4-1 to 4-n is expressed by the following formula.

$$ti = \tau i - Ti \quad (3)$$

The amount of delay previously determined by the above formulas (2) and (3) is stored in the memory (ROM) 7. The control circuit 8 reads the amount of delay from the memory to control the fine and coarse delay lines.

Figure 4:
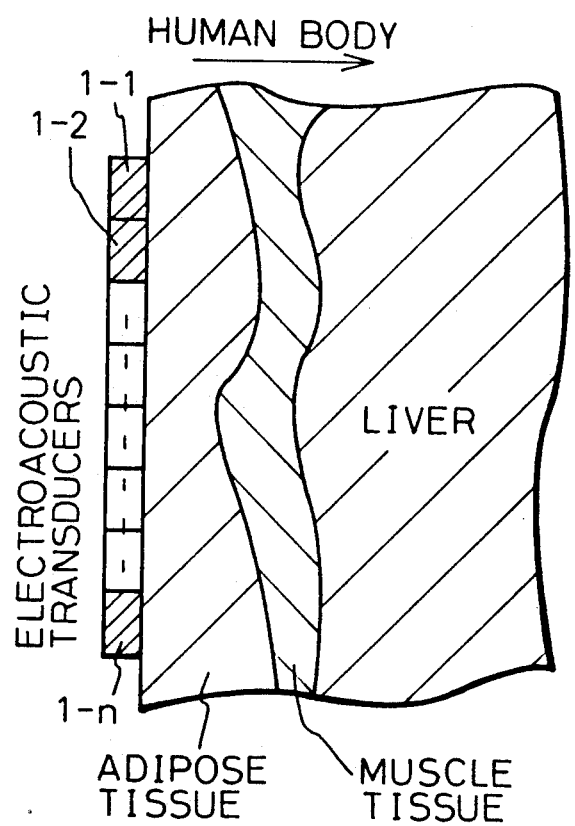
FIG. 4 is a schematic sectional view of an object.

FIG. 4 is a schematic sectional view of an object, for example, a human body. The electroacoustic transducers 1-1 to 1-n are aligned on the surface of the human body to diagnose an internal organ, for example, a liver. Of course, both adipose tissue and muscle tissue exist between the transducer and the liver. In this case, the propagation speed of the ultrasonic waves for the adipose tissue is different from that of the muscle tissue. In general, the propagation speed in the muscle and liver tissues is 1570 per second, and the propagation speed in the adipose tissue is 1480 per second. As is obvious, the former is faster than the latter within the human body. Further, as shown in the drawing, each tissue has a different thickness. Accordingly, this is the reason for nonuniformity of the propagation speed within the object and thus it is very difficult to obtain a clear and precise tomogram image of the object.

Figure 5:
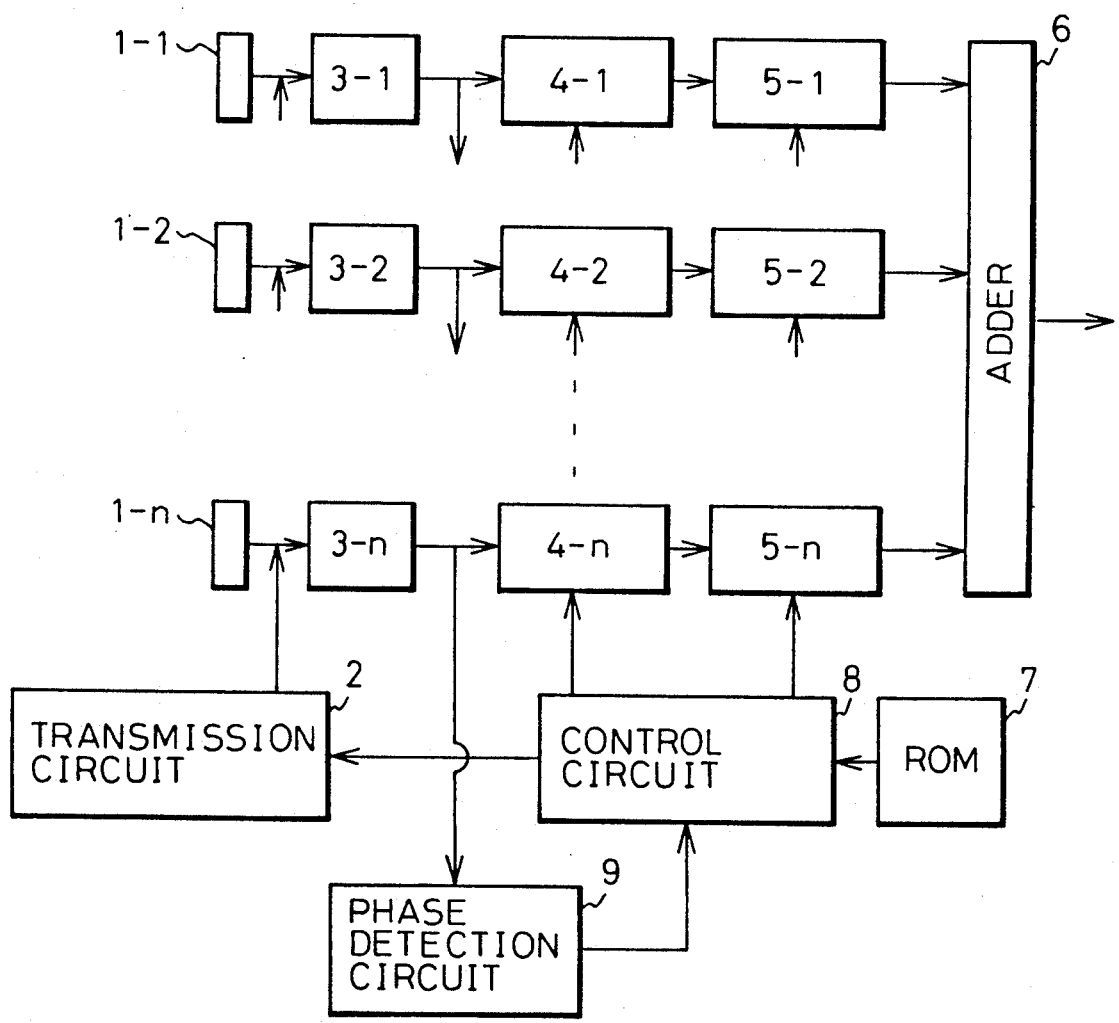
FIG. 5 is a schematic block diagram of another conventional ultrasonic imaging apparatus.

FIG. 5 is a schematic block diagram of another conventional ultrasonic imaging apparatus. This apparatus is superior to the structure shown in FIG. 1 in solving the above explained problem. The reference numbers used in FIG. 1 identify the same components in this drawing. In FIG. 5, reference number 9 denotes a phase detection circuit. The phase detection circuit 9 is added to the structure shown in FIG. 1, and detects the phase of the detection signal of each of the electroacoustic transducers 1- to 1-n and supplies resultant data to the control circuit 8 to adjust the amount of delay.

Some phase detection circuits are known in the documents, for example, U.S. Pat. No. 4,817,614, U.S. Pat. No. 4,471,785, and U.S. Pat. No. 4,484,477. The phase detection shown in the documents is explained in detail hereinafter.

Figure 6:
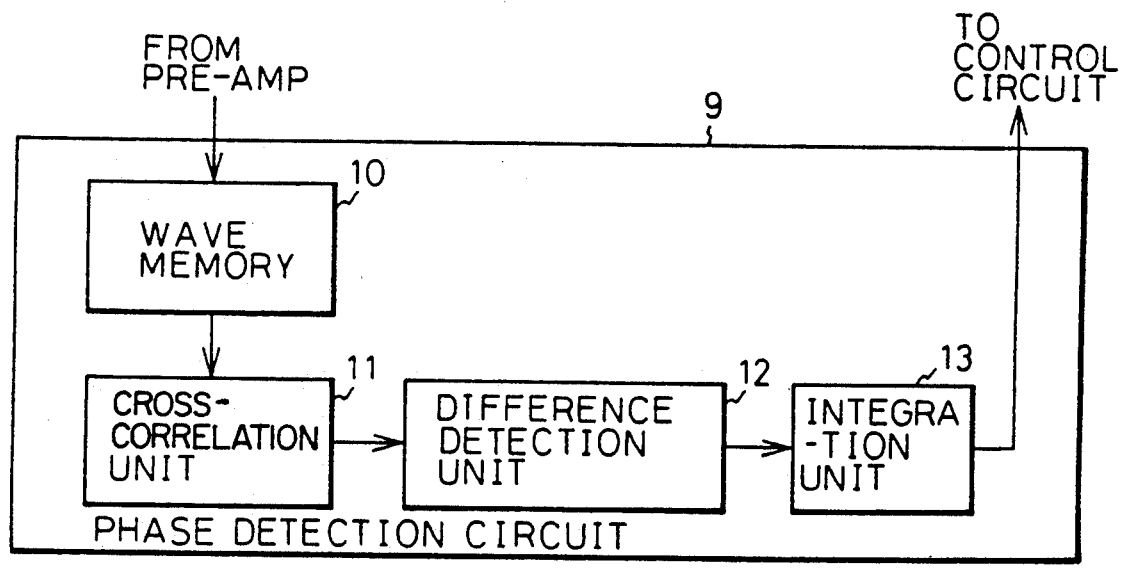
FIG. 6 is a detailed block diagram of a phase detection circuit shown in FIG. 5.

FIG. 6 is a detailed block diagram of the phase detection circuit shown in FIG. 5. In FIG. 6, reference number 10 denotes a wave memory, 11 a cross-correlation integration unit, 12 a difference detection unit, and 13 an integration unit. The wave memory 10 temporarily stores the detection signal from each pre-amplifier 3-1 to 3-n. The cross-correlation unit 11 calculates a cross-correlation value by selecting the detection signals of two adjacent electroacoustic transducers from the wave memory 10. The difference detection unit 12 detects the time difference of the maximum cross-correlation value calculated by the cross-correlation unit 11. The integration unit 13 integrates the time difference detected by the difference detection unit 12, determines the amount of delay for all detection signals, and informs the control circuit 8 of the amount of delay.

In this case, if the wave memory 10 is formed by a digital memory, it is necessary to provide an analog-to-digital converter. Further, if the wave memory comprises an analog memory, it is necessary to provide a sample-holding circuit. However, these circuits are omitted to simplify the explanation.

Figure 7:
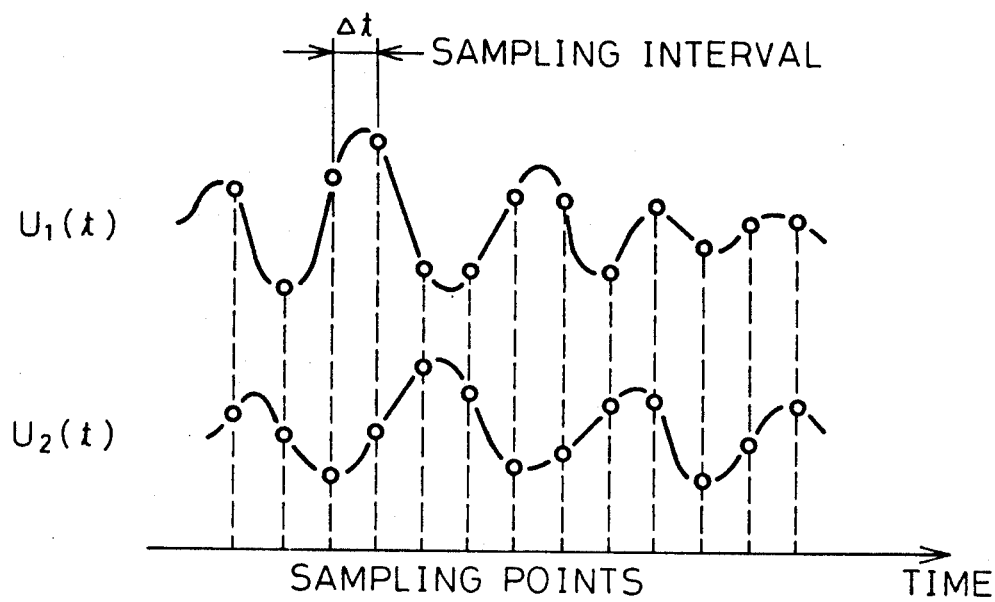
FIGS. 7 and 8 are graphs for explaining a mutual-relation value determined by the phase detection circuit shown in FIG. 6.
Figure 8:
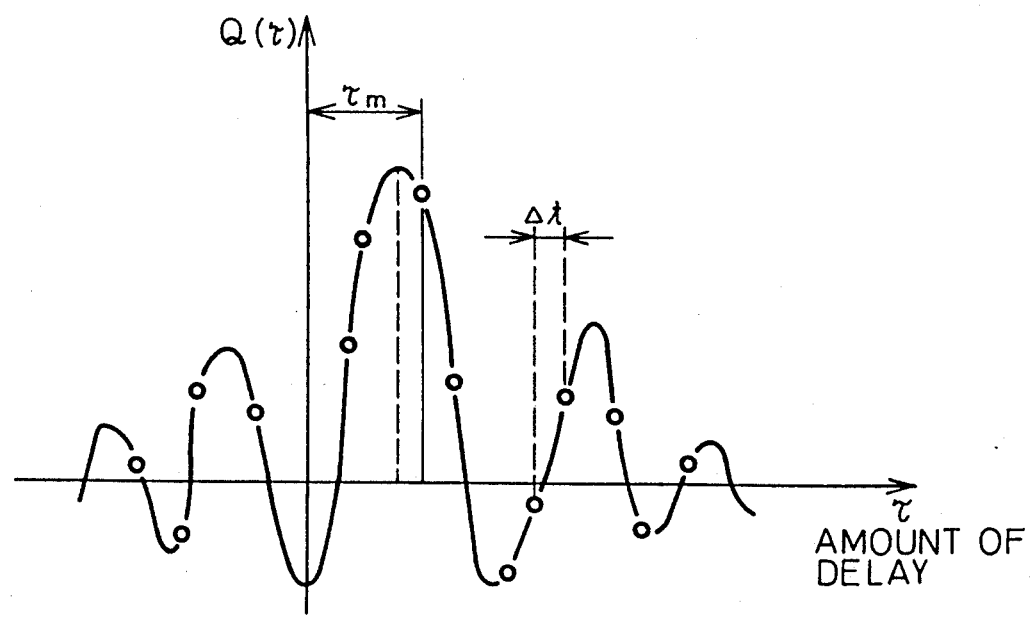

FIGS. 7 and 8 are graphs explaining the cross-correlation value determined by the phase detection circuit shown in FIG. 6. In these drawings, $u_1(t)$ and $U_2(t)$ denote the respective detection signals from two adjacent electroacoustic transducers, $\Delta t$ denotes a sampling time interval, $Q(\tau)$ denotes the cross-correlation value, and $\tau m$ denotes the maximum delay value. The cross-correlation value $Q(\tau)$ is expressed by the following formula.

$$Q(\tau) = \int_{t1}^{t2} u_1(t)u_2(t)dt \qquad (2)$$

where, t1 to t2 denotes the calculation time interval.

Based on the above formula, the cross-correlation unit 11 calculates the cross-correlation value Q($\tau i$) at each time difference (i.e., amount of delay) $\tau i$, and the difference detection unit 12 detects the maximum time difference (i.e., the maximum amount of delay) $\tau_m$ of the cross-correlation value Q($\tau_m$). Further, the integration unit 13 integrates the time difference, determines the amount of delay for all detection signals, and informs the control circuit 8.

As another known document, "U.S. Pat. No. 4,835,689" discloses a method for correcting the deterioration of the image caused by nonuniformity of the propagation speed within the object by using quadrature modulation. Further, "Phase-Aberration Correction Using Signals From Point Reflectora and Diffuse Scatterres" by S. W. Flax and M. O'Donnel, IEEE Vol. 35, No. 6, November 1988, pp 758-767 discloses an error of ultrasonic waves emitted from the electroacoustic transducer.

There are, however some problems in the above conventional ultrasonic imaging apparatus shown in FIG. 5. As explained above, the phase detection circuit 9 performs a calculation of the cross-correlation value of the detection signal to determine the amount of delay necessary to prevent deterioration of the tomogram image caused by nonuniformity of the propagation speeds within the object.

As shown in FIG. 8, however, since the cross-correlation value is calculated from the time sampling interval $\Delta t$ of the detection signal, the amount of delay determined by the phase detection circuit 9 includes an error, as contained in the same time sampling interval $\Delta t$. That is, since the amount of delay depends on the sampling time interval $\Delta t$, the error in the sampling time interval $\Delta t$ is included in the amount of delay determined by the phase detection circuit 9. Further, each error is accumulated when the integration unit 13 determines the amount of delay for all detection signals so that it is very difficult to determine a precise amount of delay of the detection signal from the electroacoustic transducers 1-1 to 1-n.

The above document of "S. W. Flax and M. O'Donnel" discloses the use of a very high sampling frequency to solve the above problem. That is, in general, when the frequency of the ultrasonic waves is 3.5 MHz, the sampling time interval $\Delta t$ is set to 20 MHz. However, in "S. W. Flax and M. O'Donnel", the sampling time interval $\Delta t$ is set to a very high frequency, for example, 100 MHz to prevent the error accumulated in the sampling time interval.

However, as is obvious, the higher the sampling frequency, the more the amount of the sampling data. Accordingly, it is necessary to provide a very large and complex phase detection circuit to process this bulky sampling data. Further, although the phase detection circuit performs a calculation of the cross-correlation for the detection signal to determine the amount of delay of the detection signal and prevent deterioration of the tomogram caused by nonuniformity of the propagation speed, this calculation of the cross-correlation requires many multiplications of the floating decimal point values in both analog and digital signals. That is, the above conventional art requires bulky hardware, particularly, a very large and complex phase detection circuit.

Therefore, the object of the present invention is to provide an ultrasonic imaging apparatus that can prevent the deterioration of the tomogram image caused by nonuniformity of the propagation speed within the object and can achieve a high precision tomogram image, and with the ultrasonic imaging apparatus having a very simplified structure.

Figure 9:
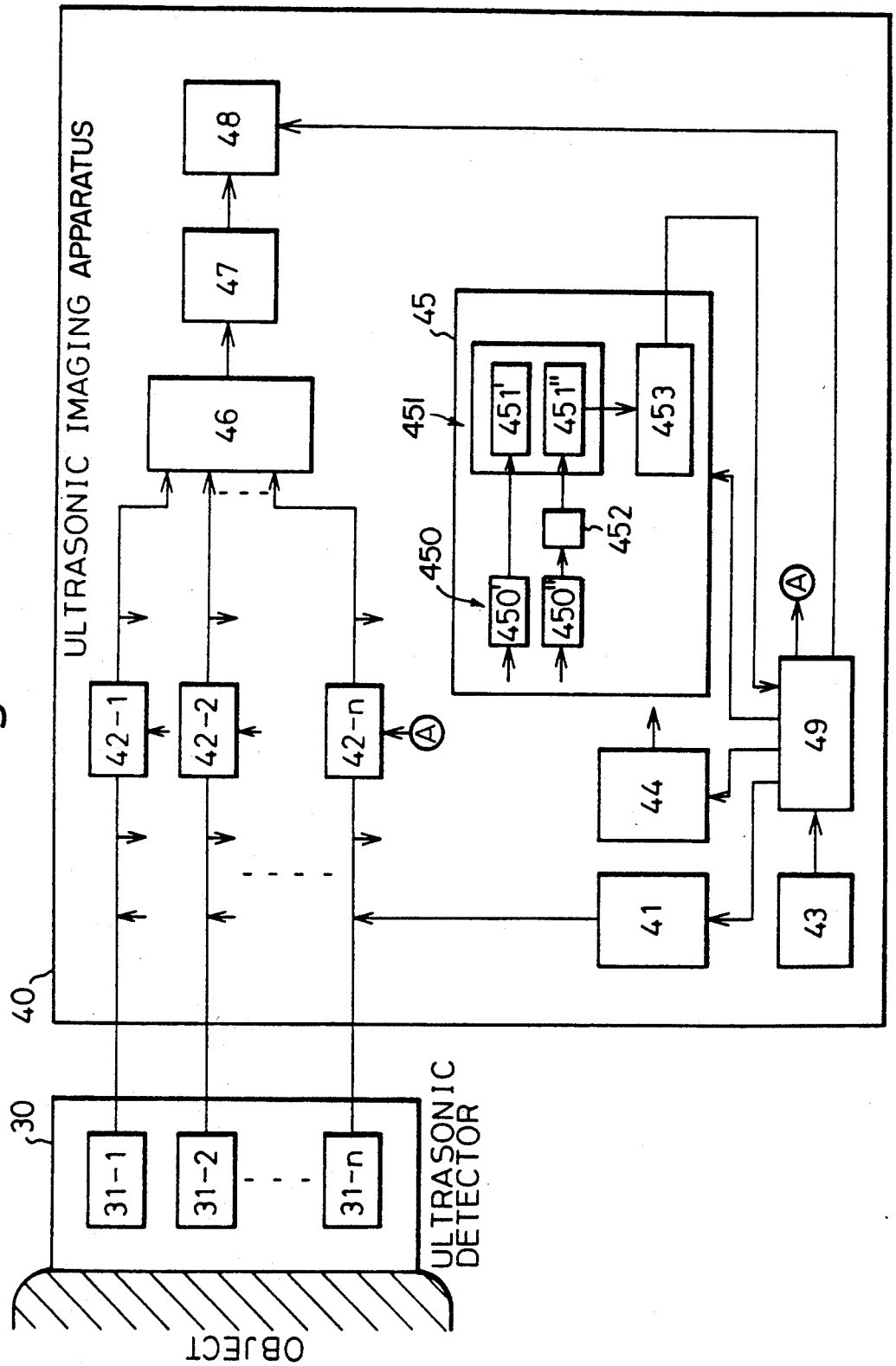
FIG. 9 is a schematic block diagram of an ultrasonic imaging apparatus according to the present invention.

FIG. 9 is a schematic block diagram of a ultrasonic imaging apparatus according to one aspect of the present invention. Briefly, an important feature of the present invention lies in the use of binary signals in the phase detection circuit.

In FIG. 9, reference number 30 denotes an ultrasonic detector formed by a plurality of electroacoustic transducers 31-1 to 31-n, and 40 denotes the basic arrangement of an ultrasonic imaging apparatus. The electroacoustic transducers 31-1 to 31-n are provided in a line (aligned) along the object to be diagnosed. The electroacoustic transducers 31-1 to 31-n emit the ultrasonic waves to the object, detect the waves reflected therefrom, and convert the reflected waves to corresponding electrical detection signals. The apparatus 40 comprises a transmission unit 41, phasing units 42-1 to 42-n, a storage (memory) unit 43, a reference signal generating unit 44, a phase detection unit 45, an adder 46, a display signal generating unit 47, a display unit 48, and a control unit 49. the phase detection unit 45 further comprises a binary circuit 450, shift register 451, input delay circuit 452 and an error detection circuit 453.

The transmission unit 41 supplies electric pulses in parallel to the electroacoustic transducers 31- to 31-n to which control the emission thereby of the ultrasonic waves. That is, the electroacoustic transducers 31-1 to 31-n emit ultrasonic waves to the object, controlled in time by the electric pulses. Each phasing unit 42-1 to 42-n performs the phasing process by delaying the detection signal from the corresponding electroacoustic transducer in accordance with the distance between the electroacoustic transducer and the object. The storage unit 43 stores the amount of delay, as previously determined, based on the distance between each of the plural electroacoustic transducers and the focused point.

The reference signal generating unit 44 generates a reference signal having the same frequency as the detection signal. The phase detection unit 45 detects the phase errors of the detection signals caused by the above-noted nonuniformity of the detection signals. The adder 46 adds all detection signals, as phased by the phasing units 42-1 to 42-n. The display signal generating unit 47 generates the display signal after converting the summation output signal of (i.e., the sum of the signals added by) the adder 46 into a brightness signal. The display unit 48 displays the tomogram image of the object. Further, the control unit 49 controls all operations of the above units 41, 43, 44, and 45.

In the phase detection unit 45, the binary circuit 450 binarizes the detection signals from each two adjacent electroacoustic transducers for the plurality thereof, thereby to detect the phase errors of their respective detection signals caused by the nonuniformity of the irpropagation speeds. In this case, the reference signal from the reference signal detection unit 44 may be used instead of one of the two detection signals. The shift register 451' sequentially shifts and latches a binary signal from the binary circuit 450'. As shown in the drawing, a pair of binary circuits 450' and 450" and a pair of shift registers 451' and 451" are provided for the shifting and latching operation. The binary circuit 450' is directly connected to the shift register 451' and the other binary circuit 450" is connected to the other shift register 451" through the input delay circuit 452, which delays the binary signal output by circuit 450'. The error detection circuit 453 detects the error of the phase of the detection signal by obtaining the cross-correlation value of the binary signals shifted by the shift registers 451' and 451". Further, although the shift registers 451' and 451" delay the respective binary signals in one direction, the input delay circuit 452 is provided for detecting an error having an inverted phase.

The error detection circuit 453 corresponds to the number of the latch of the shift register 451 and the other latch signal is delayed by the input delay circuit 452. Accordingly, the error detection circuit 453 may be formed by an adding means and a decision means. The former increases the added values accumulated thereby when these latch signals indicate the same signal level, and the latter detects the maximum added value therein.

In one aspect of the present invention, briefly, the binary circuits 450' and 450" binarize two adjacent detection signals, the shift registers 451' and 451" shift the respective two detection signals, as binarized by the binary circuits 450' and 45", in accordance with different delay times and the error detection circuit 453 calculates the cross-correlation value between the two adjacent, binarized detection signals. Further, the error detection circuit 453 determines the maximum cross-correlation delay $\tau m$ among the cross-correlation values.

In this case, when using the detection signals from the electroacoustic transducers 31-1 to 31-n, the error detection circuit 453 detects the amount of the phase delay, caused by the nonuniformity of the propagation speed, by calculating the difference value between the amount of delay of the electroacoustic transducers and the amount of delay already set in the phasing units 42-1 to 42-n. Meanwhile, when using the detection signals from the phasing units 42-1 to 42-n, the error detection circuit 453 detects the amount of the phase delay caused by the nonuniformity of the propagation speed, and the control unit 49 corrects the amount of delay, already set in the phasing unit 42-1 to 42-n in accordance with the amount of the phase delay.

Further, when the binary circuit 450 binarizes the reference signal form the reference signal generating unit 44, the error detection circuit 453 can determine the amount of delay for all detection signals without calculating the accumulated amount of delay, since the common amount of delay is detected thereby.

Accordingly, in one aspect of the present invention, since the cross-correlation values are calculated in accordance with the binary signals so that the amount of delay is determined at the phasing units 42-1 to 42-n, it is possible to simplify the circuit arrangement of the phase detection circuit. As a result, it is possible to prevent deterioration of the tomogram image caused by nonuniformity of the propagation speed of ultrasonic waves within the object.

Figure 10:
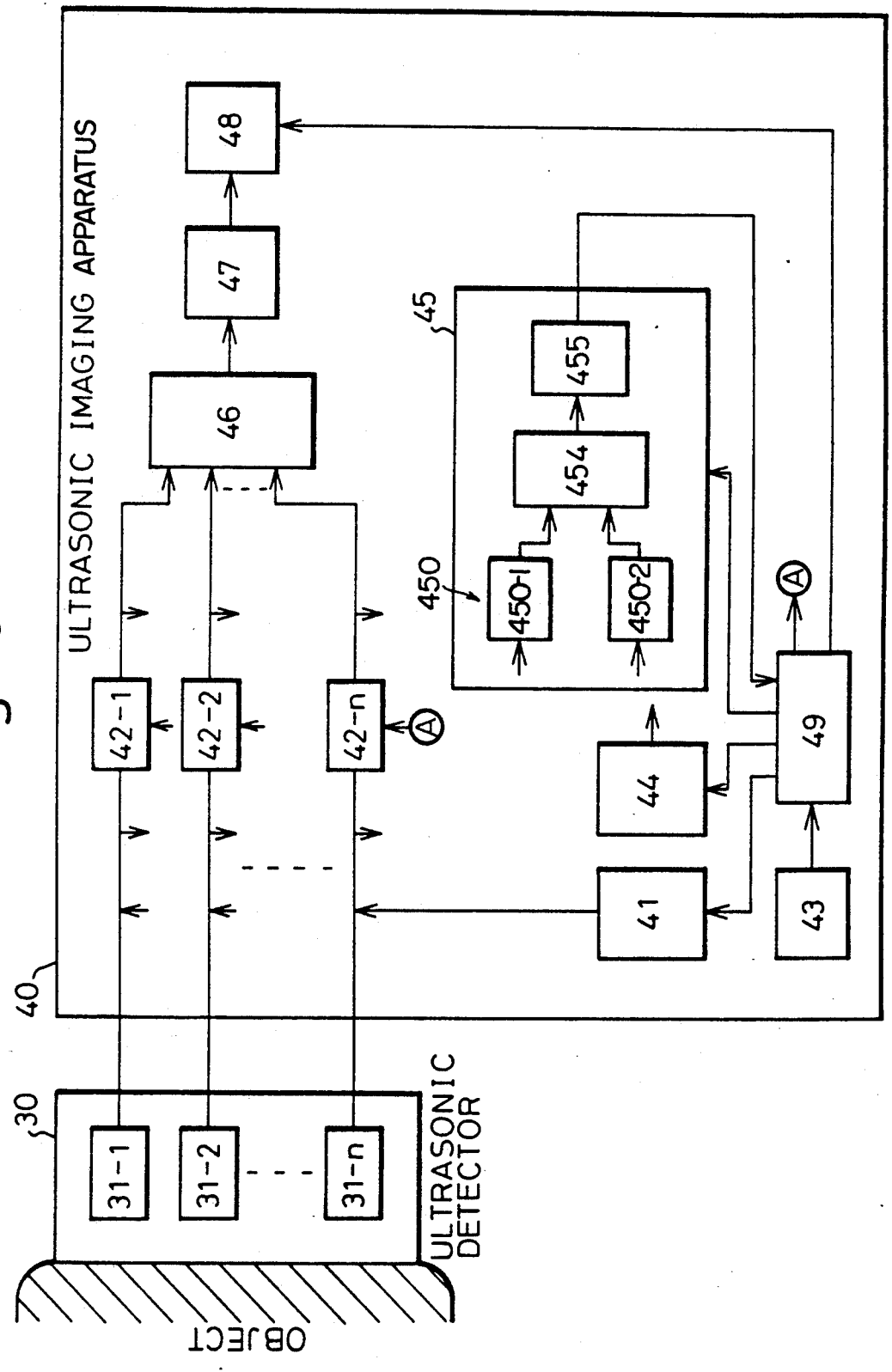
FIG. 10 is a schematic block diagram of an ultrasonic imaging apparatus according to another aspect of the present invention.

FIG. 10 is a schematic block diagram of an ultrasonic imaging apparatus according to another aspect of the present invention. The reference numbers used in FIG. 9 which are identical to those used in the prior drawings identify the same components as in the prior drawings.

In FIG. 10, the phase detection unit 45 comprises a binary circuit 450, which includes the binary circuits 450-1 and 450-2, a multiplication circuit 454 and a detection circuit 455. The multiplication circuit 454 multiplies the respective binary signals from the binary circuits 450-1 and 450-2. The detection circuit 455 detects the phase error of the detection signal by extracting the direct current components from the output of the multiplication circuit 454.

In another aspect of the present invention, briefly, the binary circuit 450 binarizes two adjacent detection signals, the multiplication circuit 454 multiplies the two detection signals, as binarized by the binary circuit 450, and generates two signal components, i.e., one signal component having double the frequency of the detection signal and the other signal component including the phase difference between the two detection signals. The amplitude level corresponding to the binary signal can be clearly determined by two signal components. The detection circuit 455 receives the two signal components and extracts the direct current component of the output signal from the multiplication circuit 454 so that the detection circuit 455 determines the difference of the amount of delay between the two adjacent detection signals.

In this case, when using the detection signals from the electroacoustic transducers 31-1 to 31-n, the detection circuit 455 detects the amount of the phase delay, caused by the nonuniformity of the propagation speed, by calculating the difference value between the amount of delay of the electroacoustic transducers and the amount of delay already set in the phasing units 42-1 to 42-n. Meanwhile, when using the detection signals from the phasing units 42-1 to 42-n, the detection circuit 455 detects the amount of the phase delay caused by the nonuniformity of the propagation speed, and the control unit 49 corrects the amount of delay already set in the phasing unit 42-1 to 42-n in accordance with the amount of the phase delay.

Further, when the binary circuit 450 binarizes the reference signal from the reference signal generating unit 44, the detection circuit 455 can determine the amount of delay for all detection signals without calculating the accumulated amount of delay since the common amount of delay is detected thereby.

Accordingly, in another aspect of the present invention, since the amount of delay of the detection signal is in accordance with the binary signals and thus the amount of delay is determined at the phasing units 42-1 to 42-n, it is possible to reduce the circuit arrangement of the phase detection circuit. As a result, it is possible to prevent deterioration of the tomogram image caused by nonuniformity of the propagation speed of ultrasonic waves within the object.

Figure 11:
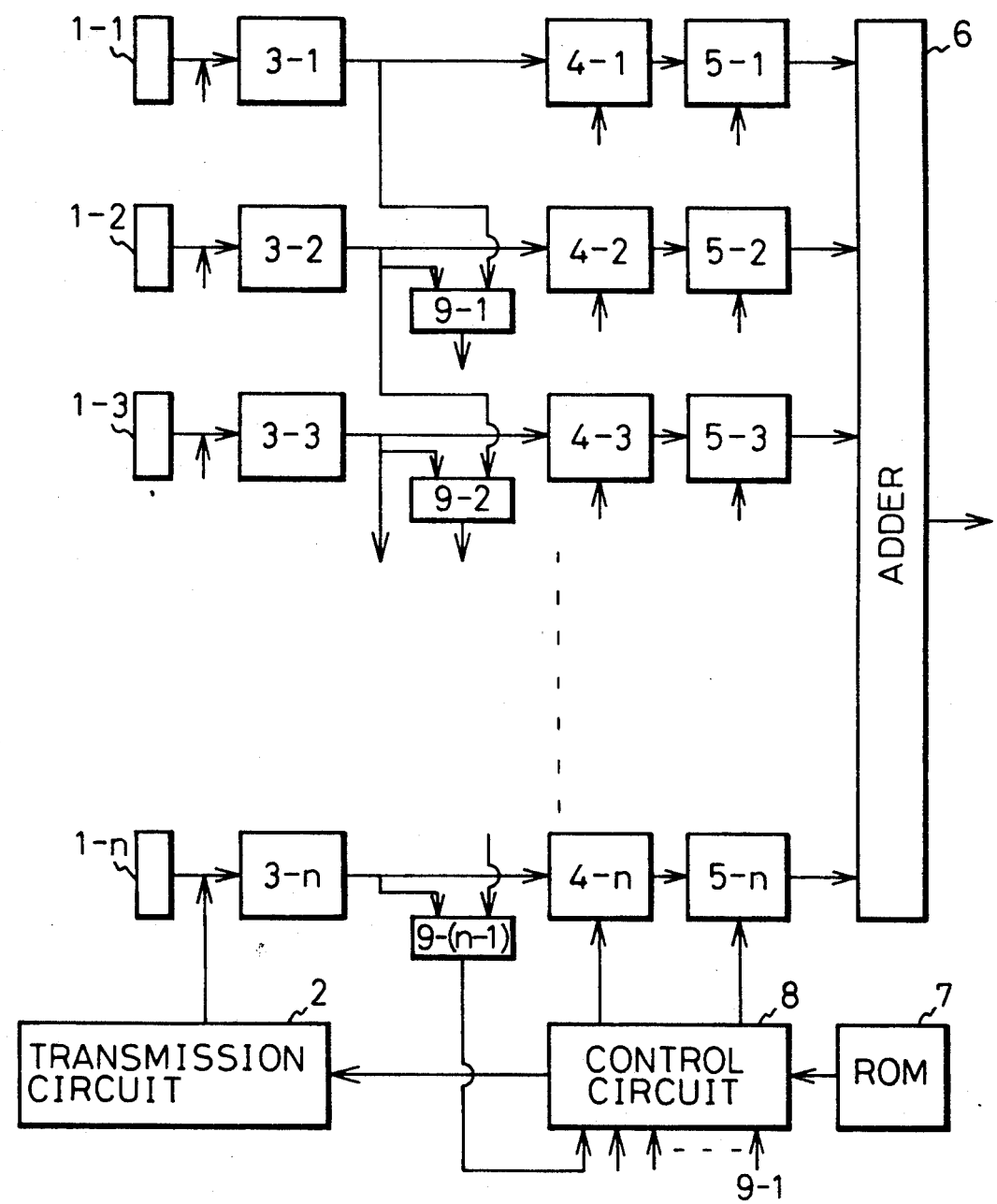
FIG. 11 is a schematic block diagram of an ultrasonic imaging apparatus according to one embodiment of the present invention.

FIG. 11 is a schematic block diagram of an ultrasonic imaging apparatus according to one embodiment of the present invention. The reference numbers used in FIG. 1 are used in FIG. 11 to identify the same components. As shown in the drawing, "n-1" phase detection circuits 9-1 to 9-(n-1) are provided in this embodiment. That is, the number of the phase detection circuits is equal to the number of the electroacoustic transducers minus one. The phase detection circuit 9-1 inputs the respective outputs of the pre-amplifiers 3-1 and 3-2. The phase detection circuit 9-2 receives as inputs the respective outputs of the pre-amplifiers 3-2 and 3-3, and the phase detection circuit 9-(n-1) receives as inputs the respective outputs of the pre-amplifiers 3-(n-1) and 3-n. That is, each phase detection circuit receives as inputs the two, respective outputs of the two, corresponding adjacent pre-amplifiers and detects the amount of delay between the respective detection signals output from those two, corresponding and adjacent pre-amplifiers. The control circuit 8 receives the respective amounts of delay, in parallel, of the phase detection circuits 9-1 to 9-(n-1), detects the error of the amounts of delay caused by the nonuniformity of the propagation speed, and corrects the deterioration of the tomogram image of the object.

Figure 12:
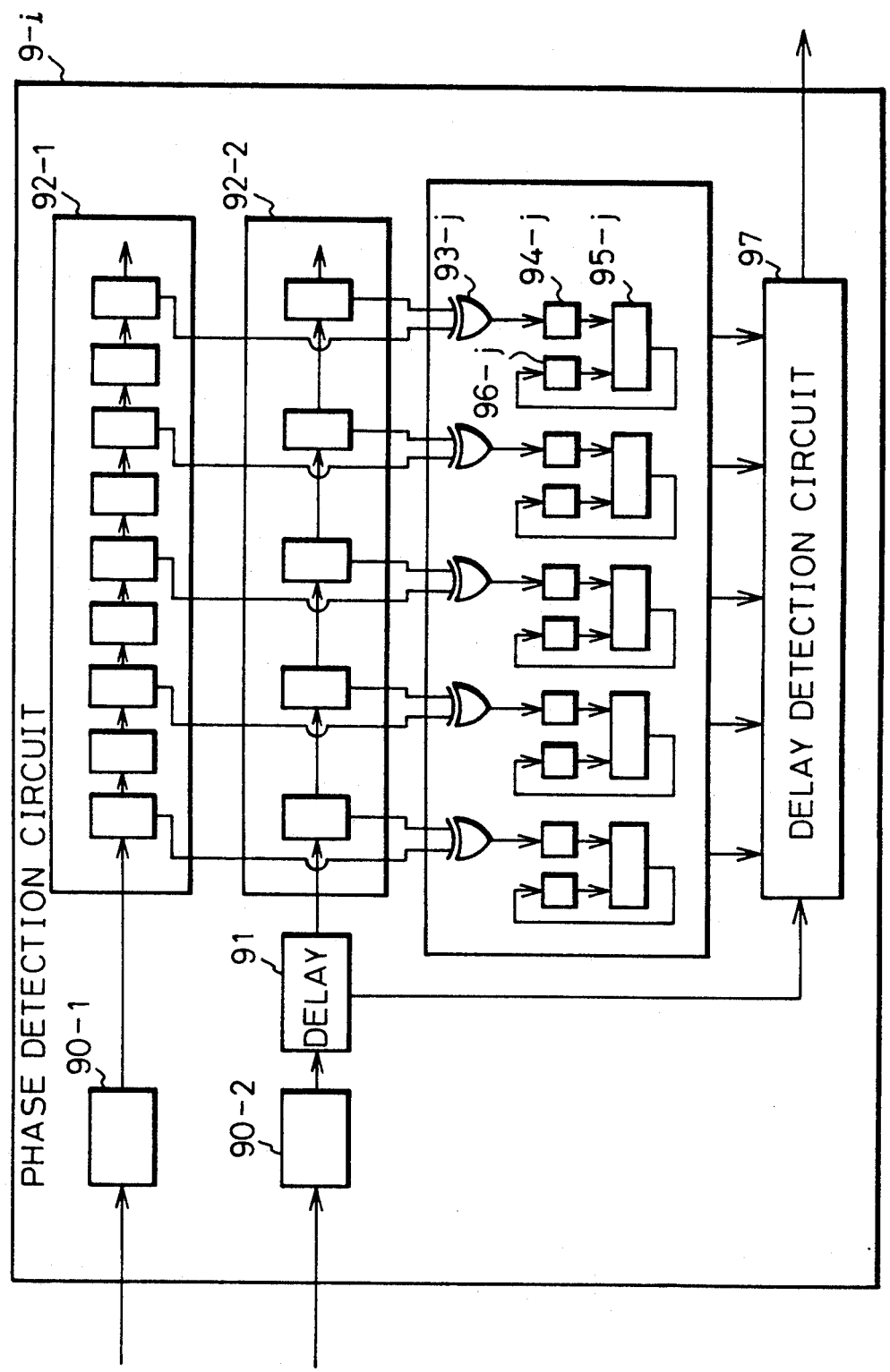
FIG. 12 is a detailed circuit of the phase detection unit shown in FIG. 11.

FIG. 12 is a detailed circuit of each phase detection unit 9-i (i.e., i=1, 2, ... (n-1)) shown in FIG. 11. In FIG. 12, reference numbers 90-1 and 90-2 denote first and second binary circuits, 91 an input delay circuit, 92-1 and 92-2 first and second shift registers, 93-j (j=1 to p) an exclusive OR circuit (EOR), 94-j a register circuit, 95-j an adder circuit, 96-j a latch circuit, and 97 a delay detection circuit.

The first and second binary circuits 90-1 and 90-2 binarize the two respective detection signals input thereto from the corresponding electroacoustic transducers 31-1 to 31-n (FIG. 10) or the phasing units 42-1 to 42-n (FIG. 10). The input delay circuit 91 is connected to the second binary circuit 90-2 and delays the binary signal output by the second binary circuit 90-2. The first shift register 92-1 inputs the successive binary signals from the first binary circuit 90-1 and sequentially latches and shifts the thus received binary signals. The second shift register 90-2 inputs the successive binary signals, each delayed by the input delay circuit 91, and sequentially latches and shifts the thus received and delayed binary signals. In this case, the latch circuits of the second shift register 92-2 are alternately provided for (i.e., they respectively correspond to only the alternate, or every other one, of the latch circuits of) the first shift register 92-1.

The exclusive OR (EOR) circuit 93-j performs an exclusive OR logic operation on the binary signals from the first shift register 92-1 and the binary signals from the second shift register 92-2. Each register circuit 94-j receives the output of the corresponding EOR circuit 93-j. The register circuit 94-j always set the logic values of "1" for the least significant bit thereof. Further, the register circuit 94-j sets the logic values of "0" for other bits, when the EOR circuit 93-j outputs the logic "1", and sets the logic "1" for other bits, when the EOR circuit 93-j outputs the logic "1". Each adder circuit 95-j receives the corresponding output of the respective register circuit 94-j and calculates accumulation values based on the received, corresponding output of the respective register 94-j. Each latch circuit 96-j feeds back the resultant output value of the respectively associated adder circuit 95-j thereby to obtain the accumulation value in the associated adder circuit 95-j. The delay detection circuit 97 detects the amount of delay of each two adjacent detections circuits by determining the latch circuit 96-j that holds the maximum value, as accumulated by the associated adder circuit 95-j. In this case, the number of the latch circuits for the first and second shift registers 92-1 and 92-2 and the number of bits for the register circuit 94-j are determined, based on (i.e., in accordance with) the calculation interval of the cross-correlation.

The operation of the phase detection circuit 9-i of FIG. 12 is explained in detail hereinafter. The binary circuits 90-1 and 90-2 receive and binarize the two detection signals respectively output by the two, corresponding and adjacent pre-amplifiers 3-(i) and 3-(i-1).

The input delay circuit 91 adjusts the binary signal output by the second binary circuit 90-2 (below, the second binary signal) to delay same relative to the binary signal output by the first binary circuit 90-1 (below, termed the "first binary signal"). Further, the succession of first binary signals is delayed relatively to the succession of second binary signals, since the latch circuits of the second shift register 92-2 are provided only alternately, relatively to those of the first shift register 92-1 (i.e., the latch circuits of 92-2 correspond respectively to only the alternate latch circuits of 92-1).

Each EOR circuit 93-j outputs logic "0" when the two respective signals received thereby from the corresponding latches of the first and second shift registers 92-1 and 92-2 indicate the same level, and outputs logic "1" when those two respective signals from the first and second shift registers 92-1 and 92-2 indicate different values. The register circuits 94-j are set to the bits "000---01", i.e., the value "1" is set in each when the corresponding EOR circuit 93-j outputs logic "0", and are set to the bits "111---11", i.e., the value "-1" is set in each thereof when the corresponding EOR circuit 93-j outputs logic "1". Each adder circuit 95-j adds the value set in the corresponding register circuit 94-j to the accumulated value latched in the associated input latch circuit 96-j.

The delay detection circuit 97 determines the latch circuit 96-j holding the maximum value and corrects the amount of delay for the input delay circuit 91 by using the maximum value determined by the latch circuit 96-j. Further, the delay detection circuit 97 informs the control unit 8 (FIG. 11) of the corrected amount of delay.

When the control unit 8 receives the corrected amount of delay, the control unit 8 sets the corrected amount of delay in the fine delay lines 4-1 to 4-n. That is the control unit 8 accumulates the amount of delay from the delay detection circuit 97 to determine the amount of delay for all detection signals. Further, the control unit 8 detects the phase error caused by the nonuniformity of the propagation speed within the object by calculating the difference between the above amount of delay and the amount of delay defined by the formula (1), and corrects the amount of delay already set in the fine delay lines 4-1 to 4-n by the corrected amount of delay.

Accordingly, in another aspect of the present invention, since the phase detection unit 9-i calculates the cross-correlation value by using the binarized detection signals and thereby determines the amount of delay for the detection signal, it is possible to simplify the circuit arrangement of the phase detection circuit.

Figure 13:
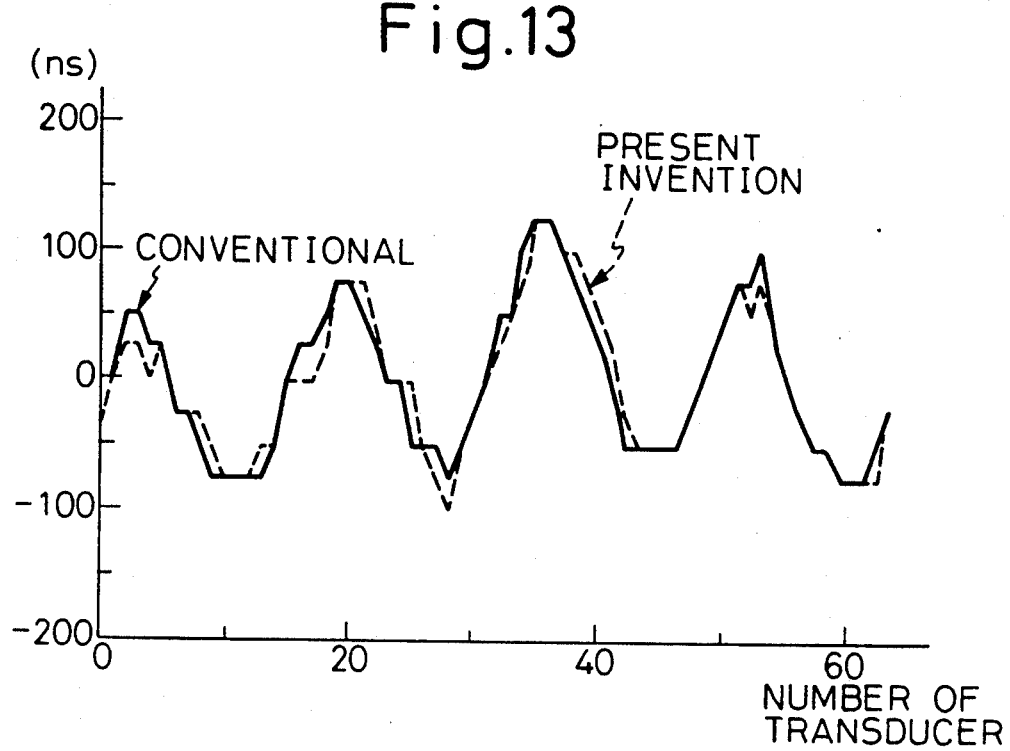
FIG. 13 is a graph for explaining the effect of the present invention.

FIG. 13 is a graph explaining the effect of the present invention. This graph compares the actual measurement value for the present invention with that of the conventional art. The ordinate denotes the amount of delay (nano-seconds, "ns") to be corrected, and the abscissa denotes the number of the electroacoustic transducers. The solid line denotes the actual measurement value of the amount of delay of the conventional art, based on the analog calculation, and the dotted line denotes the actual measurement value of the amount of delay of the present invention, based on the binary calculation. As is obvious from the graph, the dotted line is very close to the solid line so that there is no significant difference between the analog calculation and the binary calculation.

Figure 14:
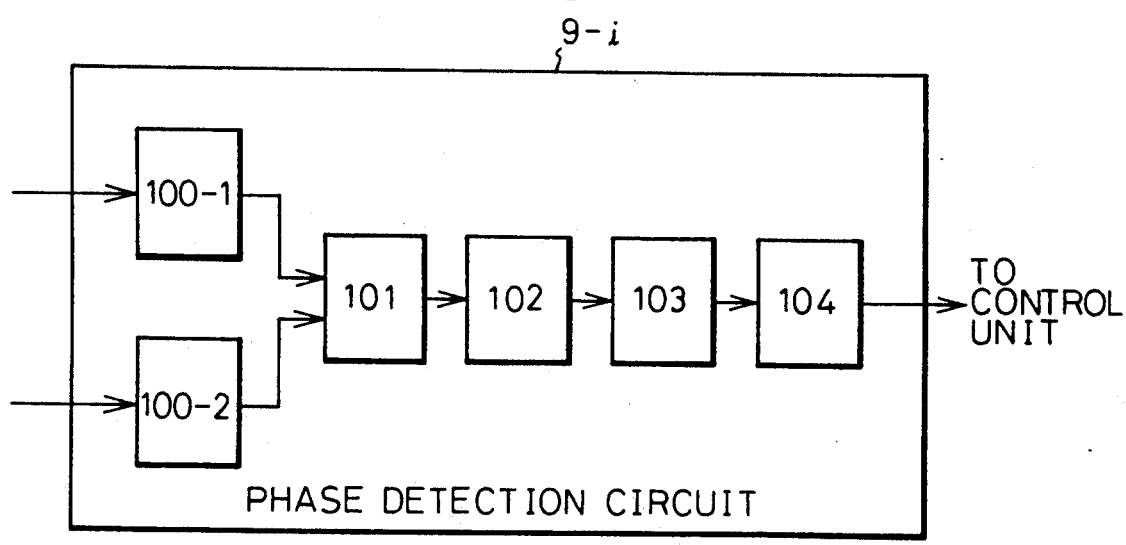
FIG. 14 is a detailed circuit block of the phase detection circuit according to another embodiment of the present invention.

FIG. 14 is a detailed circuit block diagram of the phase detection circuit according to another embodiment of the present invention. In FIG. 13, reference numbers 100-1 and 100-2 denote first and second binary circuits, 101 a multiplication circuit, 102 a low-pass filter, 103 an average value calculation circuit, and 104 a delay detection circuit.

The first and second binary circuits 100-1 and 100-2 binarize two detection signals, as before. The multiplication circuit 101 multiplies the first binary signal by the second binary signal. The low-pass filter 102 extracts the direct current component contained in the output values produced by the multiplication circuit 101. The average value calculation circuit 103 levels the signals output from the low-pass filter 102. The delay detection circuit 104 detects the amount of delay for the two detections signals in accordance with the signal output form the average value calculation circuit 103.

In this case, although the output binary signals produced by the binary circuits 100-1 and 100-2 are provided as square waves, sine waves are used for this calculation instead of the square waves to simplify the explanation. The multiplication circuit 101 performs the following calculation.

$$\sin(\omega\tau + \phi) \times \sin\omega\tau = -\tfrac{1}{2}[\cos(2\omega\tau + \phi) - \cos\omega\tau] \quad (5)$$

where, the first binary signal is "$\sin \omega\tau$", and the second binary signal is "$\sin (\omega\tau + \phi)$".

The low-pass filter 102 extracts the direct current component "$\cos \phi/2$".

The delay detection circuit 104 obtains the phase difference "$\phi$" between the two detection signals from the direct current component, as calculated and output by the average value calculation circuit 103, and converts the phase difference "$\phi$" into the amount of delay. Further, the delay detection circuit 104 transmits the resultant data, i.e., of the amount of delay, to the control unit 8. The control unit 8 detects the phase error caused by the nonuniformity of the propagation speed and corrects the amount of delay already set in the fine delay lines 4-1 to 4-n to the detected amount of delay.

Figure 15:
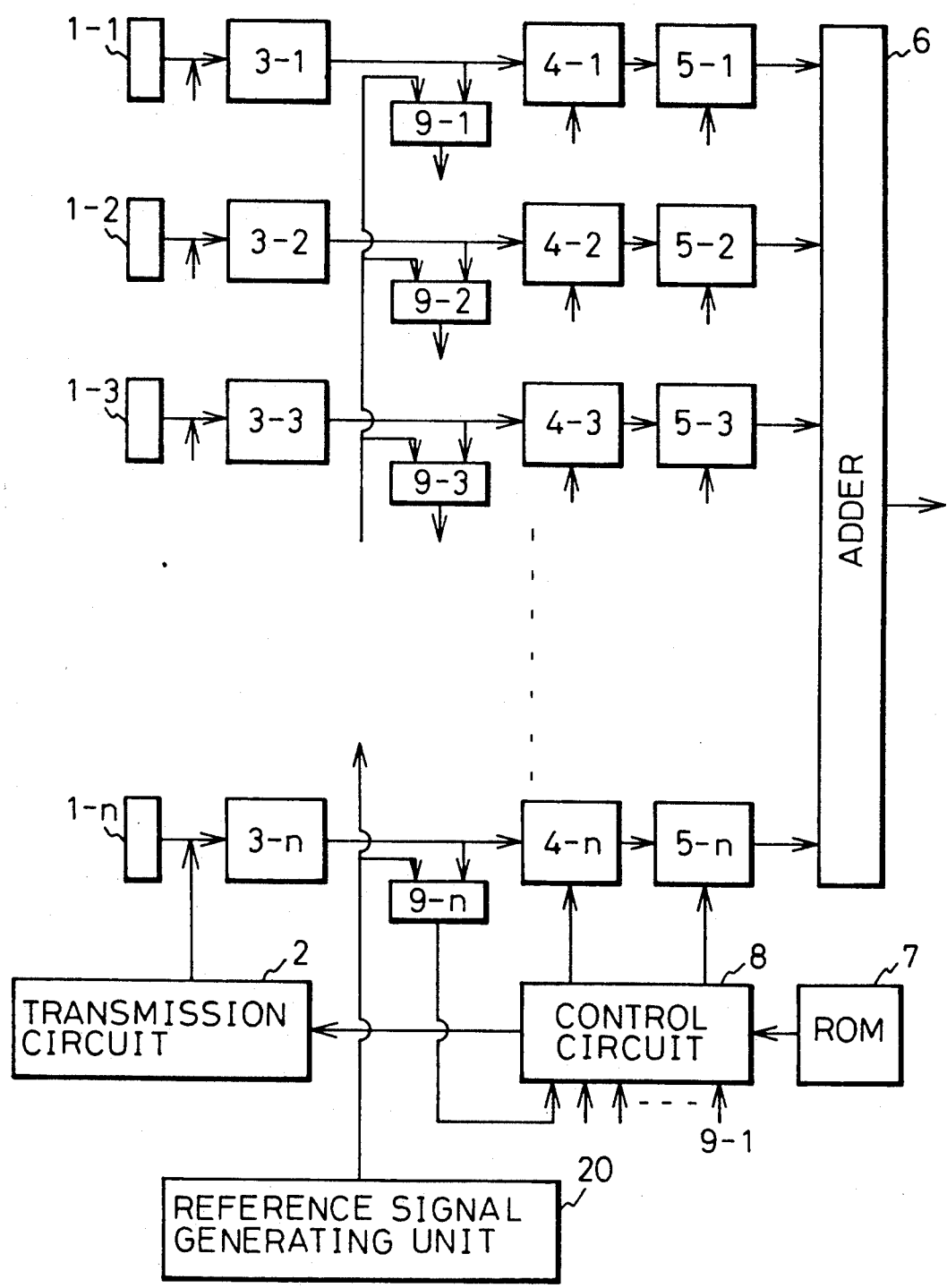
FIG. 15 is a schematic block diagram of an ultrasonic imaging apparatus according to another embodiment of the present invention.

FIG. 15 is a schematic block diagram of an ultrasonic imaging apparatus according to another embodiment of the present invention. The same reference numbers as used in FIG. 11 identify the same components in this drawing of FIG. 15. In this embodiment, the number of phase detection circuits 9-1 to 9-n is equal to that of the pre-amplifiers 3-1 to 3-n. Further, a reference signal generating unit 20 is added to the circuit shown in FIG. 11. The reference signal generating circuit 20 generates a reference signal having the same frequency as that of the detection signals output by the electroacoustic transducers 1-1 to 1-n, and outputs the reference signal, in parallel, to each of the phase detection circuits 9-i. Accordingly, each phase detection circuit 9-i receives the detection signal from the associated pre-amplifier 3-i and the reference signal from the above reference signal generating circuit 20. According to this embodiment, it is not necessary to perform the accumulation calculation, as performed and explained in relation to FIG. 11, because the amount of delay at each phasing unit is determined by comparing the corresponding binarized signal with the common reference signal.

Figure 16:
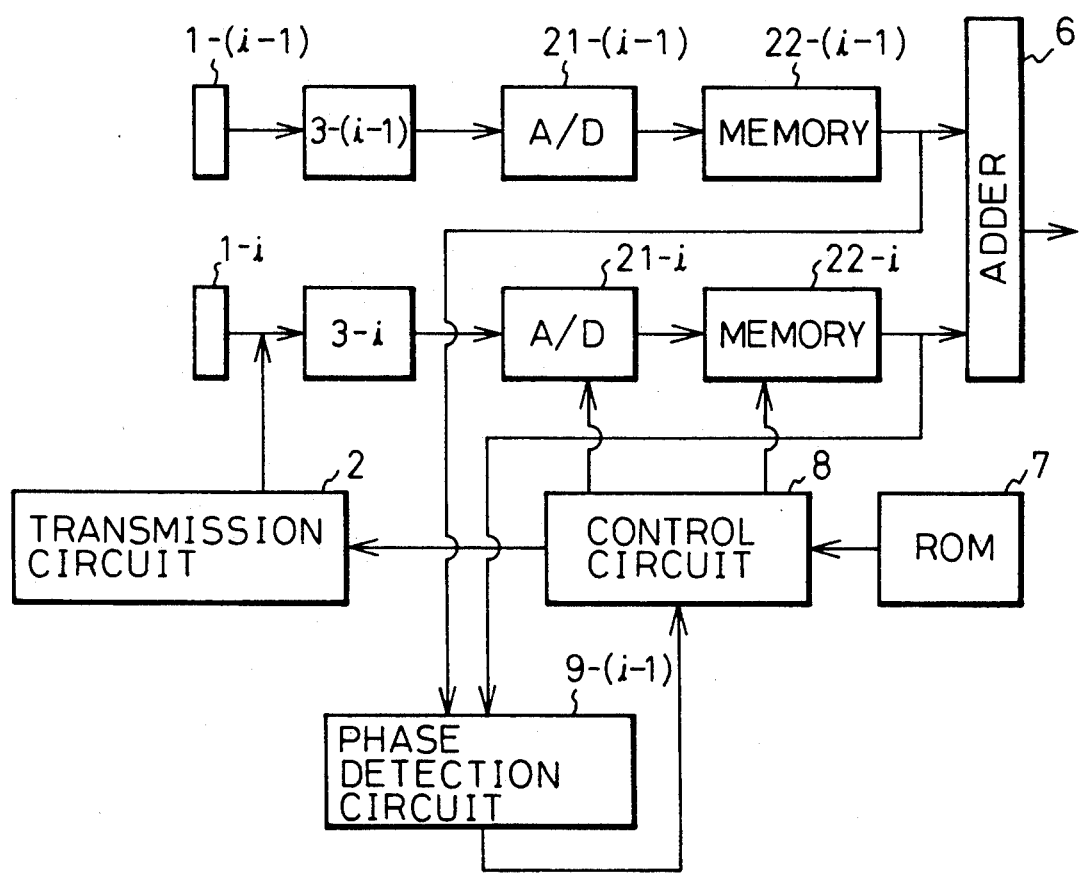
FIG. 16 is a schematic block diagram of an ultrasonic imaging apparatus according to still another embodiment of the present invention.

FIG. 16 is a schematic block diagram of an ultrasonic imaging apparatus according to still another embodiment of the present invention. In FIG. 16, reference numbers 21-(i-1) and 21-i denote analog-to-digital (A/D) converters, and 22-(i-1) and 22-i denote storage (memory) units. The A/D converters 21-(i-1) and 21-i convert the detection signals from the pre-amplifiers 3-(i-1) and 3-i to corresponding digital values, and these digital values are stored in the storage units 22-(i-1) and 22-i. The control unit 8 detects the amount of the delay by controlling the read out timing from the storage units 22-(i-1) and 22-i. In this embodiment, since the detection signals are detected for the input stage of the adder 6, the phase detection circuit 9-i can directly detect the amount of delay to be corrected so that the control unit 8 does not perform the calculation of the difference between the amount of delay from the detection signal and the amount of delay.

Figure 17A:
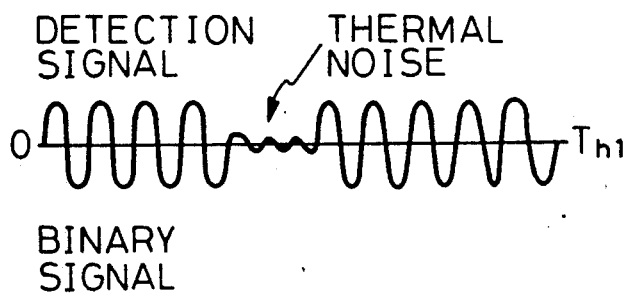
FIG. 17A is a view for explaining detection signals, thermal noise, and a threshold level at zero volt of the detection signal.
Figure 17B:
FIG. 17B is a view for explaining binary signals for the detections signals and the thermal noise shown in FIG. 17A.
Figure 18A:
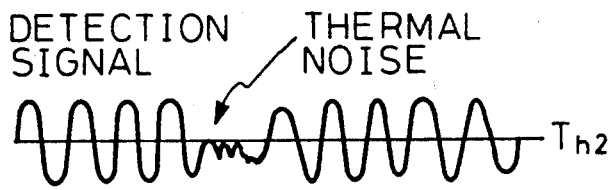
FIG. 18A is a view for explaining detection signals, thermal noise, and a threshold level according to the present invention.
Figure 18B:
FIG. 18B is a view for explaining binary signals for the detection signals and the thermal noise shown in FIG. 18A.
Figure 19A:
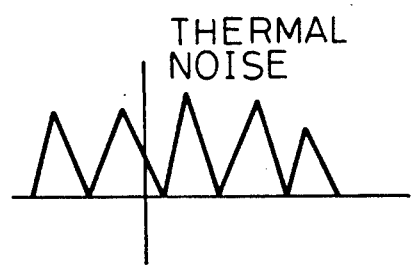
FIG. 19A is a view for explaining the thermal noise shown in FIG. 17A.
Figure 19B:
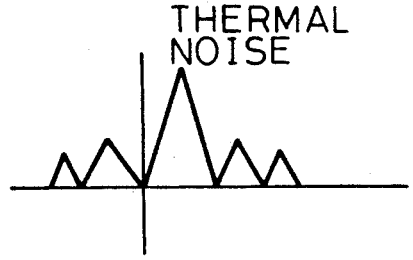
FIG. 19B is a view for explaining the thermal noise shown in FIG. 18A.

FIG. 17A is a view for explaining (analog) detection signals, (analog) thermal noise, and a threshold level Th1 at zero volts of the detection signal, and FIG. 17B is a view for explaining binary signals used for the (analog) detection signals and the (analog) thermal noise shown in FIG. 17A. Further, FIG. 18A is a view for explaining (analog) detection signals, (analog) thermal noise, and a threshold level Th2 according to the present invention, and FIG. 18B is a view for explaining binary signals used for the (analog) detection signals and the (analog) thermal noise shown in FIG. 18A. Still further, FIG. 19A is a view for explaining the thermal noise shown in FIG. 17A, and FIG. 19B is a view for explaining the thermal noise shown in FIG. 18A.

In the first and second aspects of the present invention, the first and second binary units set a threshold value, for binarizing the detection signals, which is approximately the peak of thermal noise level of the electroacoustic transducer. In this case, preferably, the first and second binary units output logic "1" when the detection signal is higher than the thermal noise level, and output logic "0" when the detection signal is equal to or lower than the thermal noise level.

This reason is explained as follows. That is, when the threshold level is set to the zero volt level of the detection signal, as shown in FIG. 17A, the thermal noises are also binarized by the binary units, as shown in FIG. 17B, so that it is difficult to obtain precise binary signals. Accordingly, in the present invention, the threshold level is set to a value which is approximately the peak of the thermal noise, as shown in FIG. 18A, so that it is possible to obtain precise, binary signals, as shown in FIG. 18B, without influence of the thermal noise.

We claim:

1. An ultrasonic imaging apparatus for obtaining a tomogram image of an object to be diagnosed on a monitor comprising:

electroacoustic transducers, adapted for positioning in aligned relationship along a surface of the object, for emitting ultrasonic waves directed toward the object, detecting the ultrasonic waves reflected therefrom and converting the reflected ultrasonic waves to, and outputting, corresponding electrical detection signals;

phasing means, operatively and respectively connected to the electroacoustic transducers, for receiving the electrical detection signals, delaying the received electrical detection signals by delay amount values, previously determined in accordance with the respective distances between the corresponding electroacoustic transducers and the object and set in the phasing means, and selectively adjusting the respective phases of the detection signals, and outputting, corresponding phase-matched detection signals;

phase detection means, operatively connected either to the electroacoustic transducers or to the phasing means, for detecting the phase errors contained in, respectively, the electrical detection signals output by the electroacoustic transducers or the phase-matched detection signals output by the phasing means, and for correcting the delay amount values previously set in the phasing means in accordance with the detected phase errors, the phase detection means further comprising first and second binary units for receiving and binarizing, respectively, the electrical detection signals or the phase-matched detection signals and thereby to detect the phase error contained in the respective, received detection signals; and adding means, operatively connected to the phasing means, for accumulating the phase-matched detection signals output by the phasing means.

2. An ultrasonic imaging apparatus as claimed in claim 1, wherein the first and second binary units further comprise means for setting a threshold value for binarizing the detection signals at approximately the peak of the thermal noise level of the electroacoustic transducer.

3. An ultrasonic imaging apparatus as claimed in claim 2, wherein each of the first and second binary units outputs a logic "1" when the detection signal is higher than the threshold value and outputs a logic "0" when the detection signal is equal to or lower than the threshold value.

4. An ultrasonic imaging apparatus as claimed in claim 1, wherein the phase detection means further comprises:

first and second shift registers respectively connected to the first and second binary units for sequentially latching and shifting the corresponding first and second binary signal outputs of the first and second binary units, the first shift register having more latch units than the second shift register; and an error detection unit for detecting mutual-relation values for the corresponding binary signals output by the first and second shift registers, and thereby for detecting the phase errors of the corresponding detection signals input to the first and second binary units whereby the phase errors of all detection signals are detected by accumulating the phase errors of all the corresponding detection signals.

5. An ultrasonic imaging apparatus as claimed in claim 4, wherein the phase detection means further comprises an input delay unit connected to the second binary unit for delaying the binary signals and outputting the delayed binary signals to the second shift register thereby to correct the phase error detected by the error detection unit in accordance with the amount of delay, of the binary signals, by the input delay unit.

6. An ultrasonic imaging apparatus as claimed in claim 4, wherein the error detection unit comprises:

adder units, corresponding, in number and respectively, to the latch units of the second shift register (92-2), receiving the respective, related latch signals from the corresponding latch units of the first and second shift registers and accumulating the received latch signals when both related latch signals indicate the same level; and a decision unit receiving the received and accumulated latch signals and determining the accumulated latch signal of the maximum value.

7. An ultrasonic imaging apparatus as claimed in claim 1, further comprising reference signal generating means (44), operatively connected to the phase detection means, for generating and supplying a reference signal to one of the first and second binary units.

8. An ultrasonic imaging apparatus for obtaining a tomogram image of an object to be diagnosed on a monitor, comprising:

electroacoustic transducers, adapted for positioning in aligned relationship along a surface of the object, for emitting ultrasonic waves directed toward the object, detecting the ultrasonic waves reflected therefrom and converting the reflected ultrasonic waves to, and outputting, corresponding electrical detection signals having a first frequency;

phasing means, operatively and respectively connected to the electroacoustic transducers, for receiving the electrical detection signals, delaying the received electrical detection signals by delay amount values, previously determined in accordance with the respective distances between the corresponding electroacoustic transducers and the object and set in the phasing means, and selectively adjusting the respective phases of the detection signals, and outputting, corresponding phase-matched detection signals having a frequency common to the first frequency;

reference signal generating means (44) operatively connected to the phase detection means for generating a reference signal having the common frequency of the detection signals;

phase detection means, receiving the reference signal and operatively connected either to the electroacoustic transducers or to the phasing means, for detecting, relatively to the reference signal, the phase errors contained in, respectively, the electrical detection signals output by the electroacoustic transducers or the phase-matched detection signals output by the phasing means, relatively to the reference signal, and for correcting the delay amount values previously set in the phasing means in accordance with the detected phase errors; and adding means, operatively connected to the phasing means, for accumulating the phase-matched detection signals output by the phasing means.

9. An ultrasonic imaging apparatus as claimed in claim 8, wherein the first and second binary units further comprise means for setting a threshold value selected for binarizing the received, selected detection signals at approximately the peak of the thermal noise level of the electroacoustic transducer.

10. An ultrasonic imaging apparatus as claimed in claim 9, wherein each of the first and second binary units outputs a logic "1" when the detection signal is higher than the threshold value thermal noise level, and outputs a logic "0" when the detection signal is equal to or lower than the threshold value.

11. An ultrasonic imaging apparatus as claimed in claim 8, wherein the phase detection means further comprises:

a first binary unit for receiving either an output detection signal or a phase-matched detection signal and a second binary unit for receiving the reference signal, each binary unit binarizing the corresponding, received signal and thereby to detect the phase error contained in the detection signal received by the first binary unit;

a multiplication unit (454) operatively connected to the first and second binary units for multiplying the respective signals output by the first and second binary units; and detection means (455) operatively connected to the multiplication unit for extracting direct current components contained in the output of the multiplication unit.

* * * * *

UNITED STATES PATENT AND TRADEMARK OFFICE
CERTIFICATE OF CORRECTION

PATENT NO. : 5,235,983
DATED : Aug. 17, 1993
INVENTOR(S) : IIDA et al.

It is certified that error appears in the above-indentified patent and that said Letters Patent is hereby corrected as shown below:

Col. 8,  line 63, change "the" (second occurrence) to --their--;
         line 64, change "irpropagation" to --propagation--.

Col. 9,  line 28, change "45'''" to --450''--;
         line 50, change "form" to --from--.

Col. 11, line 42, change "set" to --sets--.

Col. 13, line 16, change "form" to --from--.

Signed and Sealed this

Second Day of August, 1994

Attest:

BRUCE LEHMAN

Attesting Officer              Commissioner of Patents and Trademarks